United States Patent
Zhang et al.

(10) Patent No.: US 11,596,598 B2
(45) Date of Patent: Mar. 7, 2023

(54) CHLOROGENIC ACID-CONTAINING COMPOSITION FOR NASAL ADMINISTRATION

(71) Applicant: SICHUAN JIUZHANG BIOLOGICAL SCIENCE AND TECHNOLOGY CO., LTD, Sichuan (CN)

(72) Inventors: Jie Zhang, Sichuan (CN); Wang Huang, Sichuan (CN); Fei Zhang, Sichuan (CN); Ya Zhang, Sichuan (CN)

(73) Assignee: SICHUAN JIUZHANG BIOLOGICAL SCIENCE AND TECHNOLOGY CO., LTD., Sichuan (CN)

( * ) Notice: Subject to any disclaimer, the term of this patent is extended or adjusted under 35 U.S.C. 154(b) by 0 days.

(21) Appl. No.: 17/060,593

(22) Filed: Oct. 1, 2020

(65) Prior Publication Data
US 2021/0251891 A1    Aug. 19, 2021

(30) Foreign Application Priority Data
Aug. 23, 2019    (CN) .......................... 201910786395.5

(51) Int. Cl.
| | | |
|---|---|---|
| A61K 9/00 | (2006.01) | |
| A61P 35/00 | (2006.01) | |
| A61K 9/51 | (2006.01) | |
| A61K 31/225 | (2006.01) | |
| A61K 47/06 | (2006.01) | |
| A61K 47/10 | (2017.01) | |
| A61K 47/12 | (2006.01) | |
| A61K 47/18 | (2017.01) | |
| A61K 47/22 | (2006.01) | |
| A61K 47/24 | (2006.01) | |
| A61K 47/32 | (2006.01) | |
| A61K 47/36 | (2006.01) | |
| A61K 47/38 | (2006.01) | |
| A61K 47/40 | (2006.01) | |

(52) U.S. Cl.
CPC .......... *A61K 9/0043* (2013.01); *A61K 9/5123* (2013.01); *A61K 9/5138* (2013.01); *A61K 9/5161* (2013.01); *A61K 31/225* (2013.01); *A61K 47/06* (2013.01); *A61K 47/10* (2013.01); *A61K 47/12* (2013.01); *A61K 47/183* (2013.01); *A61K 47/22* (2013.01); *A61K 47/24* (2013.01); *A61K 47/32* (2013.01); *A61K 47/36* (2013.01); *A61K 47/38* (2013.01); *A61K 47/40* (2013.01); *A61P 35/00* (2018.01)

(58) Field of Classification Search
CPC ..... A61P 35/00; A61K 9/0043; A61K 9/5123; A61K 9/5138; A61K 9/5161; A61K 31/225; A61K 47/06; A61K 47/10; A61K 47/12; A61K 47/183; A61K 47/22; A61K 47/24; A61K 47/32; A61K 47/36; A61K 47/38; A61K 47/40
See application file for complete search history.

(56) References Cited

FOREIGN PATENT DOCUMENTS

CN    105902525    *    8/2016    ........... A61K 9/1075

OTHER PUBLICATIONS

Martin J Donovan, et al, Dry Powder Inhaler Device Influence on Carrier Particle Performance, 101 J Pharma. Sci. 1097 (Year: 2012).*
CN 105902525 Machine translation (Year: 2016).*

* cited by examiner

*Primary Examiner* — Sean M Basquill
(74) *Attorney, Agent, or Firm* — Novick, Kim & Lee, PLLC; Allen Xue

(57) ABSTRACT

An anti-tumor composition for nasal administration has chlorogenic acid as an active ingredient, with the addition of pharmaceutically acceptable excipients or auxiliary ingredients. The chlorogenic acid preparation can improve the bioavailability of chlorogenic acid for nasal administration, penetrate the blood-brain barrier, have a significant inhibitory effect on brain tumors and nasopharyngeal carcinoma, and possess a clinical application value.

9 Claims, 2 Drawing Sheets

CHLOROGENIC ACID-CONTAINING COMPOSITION FOR NASAL ADMINISTRATION

TECHNICAL FIELD

The present invention relates to a chlorogenic acid-containing composition for nasal administration.

BACKGROUND ART

Nasal cavity, as an administration route for systemic therapy, is a very active research hotspot, and especially for protein and peptide drugs, nasal administration may become an effective method to replace injection used for a long time. In addition, the nasal mucosa is an effective way to achieve brain-targeted drug delivery. Compared with the method of oral administration and injection, nasal administration has many characteristics: (1) The method is simple, with a good compliance, and the patient can complete the medication by himself. Even when the patient cannot take the drug by himself, the family can also help to perform the administration of drug; (2) After it is administered through the nasal cavity, the drug can have a local effect, and it can also be absorbed through the nasal mucosa into the systemic circulation and reach the brain; (3) The drug can have a fast onset and be rapidly absorbed; (4) The drug avoids the first pass effect caused by oral administration and has high bioavailability.

Chlorogenic acid, as a depside originated from caffeic acid and quinic acid, is a phenylpropanoid compound produced by the shikimic acid pathway during aerobic respiration of plants. It is an important biologically active substance, and has actions such as antibacterial, antiviral, increasing white blood cell, protecting liver and choleretics, anti-tumor, lowering blood pressure and fat, scavenging free radicals, exciting the central nervous system and so on. Chlorogenic acid contains polar groups of five hydroxyls and one carboxyl, and this feature of molecular structure determines that oral administration is prone to degradation and leads to a low bioavailability. Therefore, most of the drug development focusing on chlorogenic acid is based on injections, and a small number of them use techniques such as structural modification to improve the oral bioavailability of chlorogenic acid, and significant effects have also been obtained.

At present, clinical progress on chlorogenic acid has been made in the anti-tumor field, and chlorogenic acid for injection developed by the prior company is in clinical phase II/III research. In addition, there are no other formulations of chlorogenic acid used for anti-tumor on the market or in clinical research. Patent CN 105147656A provides a chlorogenic acid preparation for nasal administration, that has a simple formula. Although the content of chlorogenic acid is high, but the nasal absorption rate is low, and it can only be used to treat allergic rhinitis.

CONTENT OF THE INVENTION

In order to solve the above technical problems, the present invention provides a anti-tumor composition for nasal administration, which is a preparation obtained by using chlorogenic acid as the active ingredient, with the addition of pharmaceutically acceptable excipients or auxiliary ingredients.

Further, said preparation is nasal powder, aerosol, or spray.

Still further, the excipients of said nasal powder are adhesive and absorption enhancer.

Further, the raw and auxiliary materials of said nasal powder are 10-90 parts of chlorogenic acid, 5-80 parts of adhesive, and 0-70 parts of absorption enhancer.

Still further, said adhesive is selected from any one or more of carbomer, chitosan, polyvinylpyrrolidone, hydroxypropylcellulose, and sodium carboxymethylcellulose; the absorption enhancer is selected from any one or more of lecithin, β-cyclodextrin, and cholic acid sodium.

Still further, the particle size of said nasal powder is 20-100 μm.

Further, the excipients of said aerosol are propellant, cosolvent and absorption enhancer.

Still further, the excipients of said aerosol are 5-30 parts by weight of propellant, 10-50 parts of cosolvent, and 1-10 parts of absorption enhancer.

Still further, said propellant is selected from any one or more of dichlorodifluoromethane, trichlorofluoromethane, heptafluoropropane, tetrafluoroethane, and dimethyl ether; the cosolvent is selected from any one or more of ethanol, glycerin, and propylene glycol; the absorption enhancer is selected from any one or more of azone, sodium ethylenediaminetetraacetate, oleic acid, lauric acid, and lauryl sulfate.

Further, the excipient of said aerosol also includes water for injection.

Further, the aerosol contains 0.1-1 g chlorogenic acid per 1 mL.

Further, the excipient of said spray is a solvent.

Still further, the solvent is selected from physiological saline and/or water for injection.

Further, the excipients of said spray also contain polyethylene glycol.

Still further, the mass ratio of polyethylene glycol to chlorogenic acid is 2:1.

Further, the spray contains 0.1-1 g chlorogenic acid per 1 mL.

The present invention also provides a method for preparing the composition mentioned above, that contains the following steps:

The absolute ethanol or aqueous ethyl acetate is added to the mixture of chlorogenic acid and the absorption enhancer to dissolve, followed by drying and pulverization, then adhesive is added, and the mixture is thoroughly mixed and passed through a 120-1000 mesh sieve to obtain the composition; or Chlorogenic acid, absorption enhancer, and adhesive are mixed, and passed through a 120-1000 mesh sieve to obtain the composition; or Chlorogenic acid, cosolvent and a small amount of solvent are heated to dissolve, and then cooled, to which are further added propellant, absorption enhancer and remaining solvent to dissolve, followed by filtration, and the filtrate is collected to obtain the composition; or Chlorogenic acid, polyethylene glycol and a small amount of solvent are heated to dissolve, and then cooled, to which is added the remaining solvent, mixed, filtered, and the filtrate is collected to obtain the composition.

The present invention also provides the use of the composition mentioned above in the preparation of a drug for improving the permeability of the blood-brain barrier of chlorogenic acid.

Further, said drug is those for alleviation and/or treatment of nasopharyngeal carcinoma or brain tumor.

Still further, said brain tumors are malignant.

Still further, said malignant brain tumors are glioblastoma, ependymoma, or oligodendrocytoma.

The present invention provides a chlorogenic acid preparation for nasal administration, which can improve the bioavailability of chlorogenic acid for nasal administration, penetrates the blood-brain barrier, has a significant inhibitory effect on brain tumors and nasopharyngeal carcinoma, and can also increase the efficacy of chlorogenic acid in the treatment of corresponding indications (such as autoimmune diseases, neurodegenerative diseases, etc.).

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

Example 1 Nasal Powder

Figure 1:
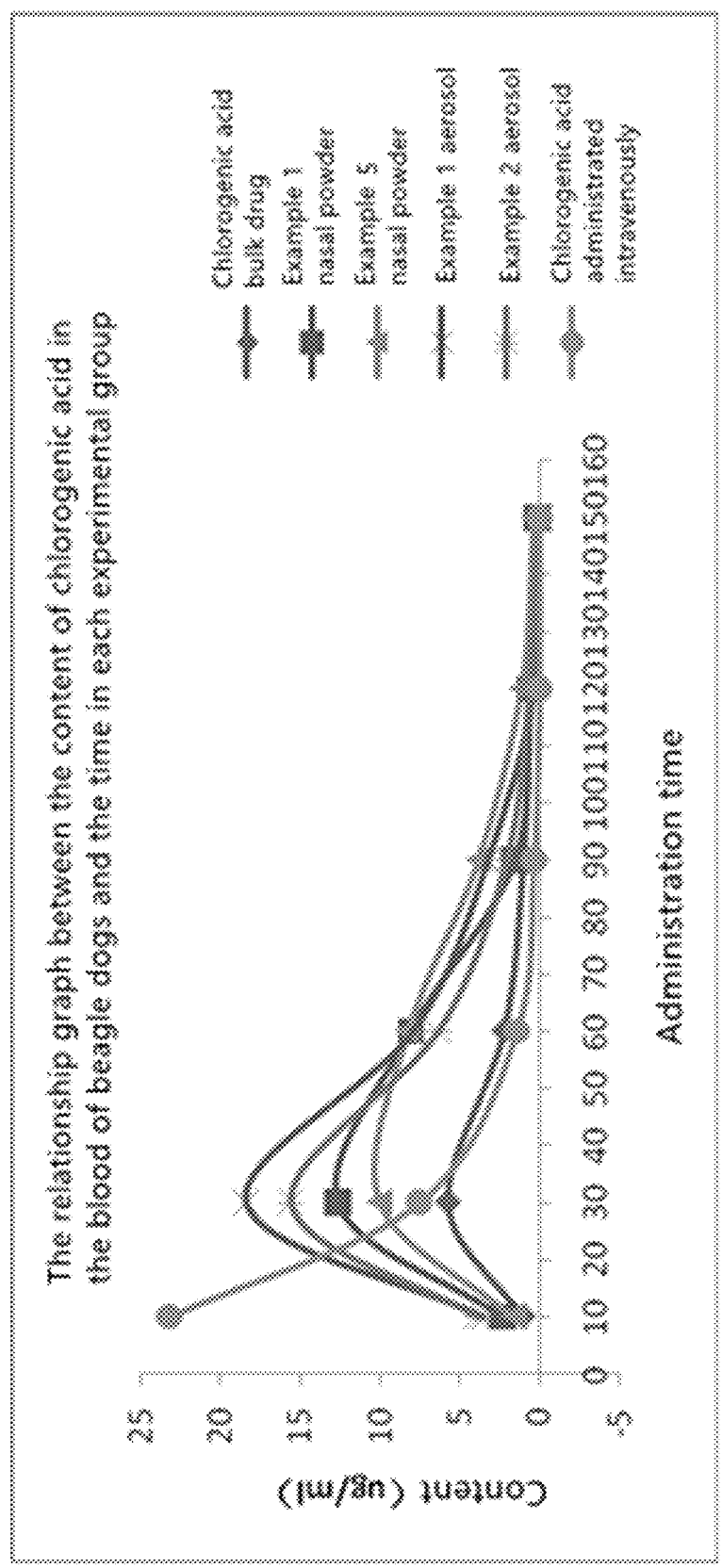
FIG. 1 shows the content of chlorogenic acid in the blood of beagle dogs time at various time points after the administration of the drugs.

| Formula | |
|---|---|
| Chlorogenic acid | 20 g |
| Lecithin | 70 g |
| Carbomer | 5 g |
| Chitosan | 5 g |

Preparative Method:

Chlorogenic acid and lecithin were weighed and dissolved in aqueous ethyl acetate under heating. The solution was stirred, and ethyl acetate was recovered under negative pressure. The residue was dried and pulverized, then carbomer and chitosan were added and mixed. The mixture was passed through a 120-mesh sieve, and subjected to a powder sprayer, to provide the nasal powder.

Example 2 Nasal Powder

| Formula | |
|---|---|
| Chlorogenic | 30 g |
| β-cyclodextrin | 60 g |
| Hydroxylpropyl cellulose | 5 g |
| Polyvinylpyrrolidone | 5 g |

Preparative Method:

Chlorogenic acid and β-cyclodextrin were weighed and dissolved in absolute ethanol under heating. The solution was stirred, and ethanol was recovered under negative pressure. The residue was dried and pulverized, then hydroxylpropyl cellulose and polyvinylpyrrolidone were added and mixed. The mixture was passed through a 120-mesh sieve, and subjected to a powder sprayer, to provide the nasal powder.

Example 3 Nasal Powder

| Formula | |
|---|---|
| Chlorogenic acid | 60 g |
| Carbomer | 20 g |
| Sodium carboxymethyl cellulose | 15 g |
| Sodium cholate | 5 g |

Preparative Method:

All materials were weighed, mixed, passed through a 150-mesh sieve, and then subjected to a powder sprayer, to provide the nasal powder.

Example 4 Nasal Powder

| Formula: | |
|---|---|
| Chlorogenic acid | 80 g |
| Sodium carboxymethyl cellulose | 15 g |
| Carbomer | 5 g |

Preparative Method:

All materials were weighed, mixed, passed through a 1000-mesh sieve, and then subjected to a powder sprayer, to provide the nasal powder.

Example 5 Nasal Powder

| Formula: | |
|---|---|
| Chlorogenic acid | 90 g |
| Polyvinylpyrrolidone | 5 g |
| Sodium cholate | 5 g |

Preparative Method:

All materials were weighed, mixed, passed through a 500-mesh sieve, and then subjected to a powder sprayer, to provide the nasal powder.

Example 6 Aerosol

| Formula | |
|---|---|
| Chlorogenic acid | 20 g |
| Ethanol | 10 g |
| Glycerol | 10 g |
| Azone | 5 g |
| Dichlorodifluoromethane | 30 g |
| Dilution to 100 mL using water for injection. | |

Preparative Method:

Chlorogenic acid, ethanol, and a small amount of injectable water were weighed and allowed to dissolve under heating, followed by cooling. The remaining materials were added, and then diluted to 100 mL with injectable water. The solution was dissolved, filtered, and the filtrate was placed into a special bottle for nasal aerosol.

Example 7 Aerosol

| Formula | |
| --- | --- |
| Chlorogenic acid | 50 g |
| Ethanol | 20 g |
| Propylene glycol | 5 g |
| Sodium ethylenediaminetetraacetate | 3 g |
| Oleic acid | 2 g |
| Trichlorofluoromethane | 20 g |
| Dilution to 100 mL with water for injection | |

Preparative Method:

Chlorogenic acid, ethanol, and a small amount of injectable water were weighed and allowed to dissolve under heating, followed by cooling. The remaining materials were added, and then diluted to 100 mL with injectable water. The solution was dissolved, filtered, and the filtrate was placed into a special bottle for nasal aerosol.

Example 8 Formula for Spray

| Formula | |
| --- | --- |
| Chlorogenic acid | 10 g |
| Polyethylene glycol | 20 g |
| Dilution to 100 mL with water for injection | |

Preparative Method:

Chlorogenic acid, polyethylene glycol, and a small amount of injectable water were weighed according to the formula, and allowed to dissolve under heating, followed by cooling. The resultant solution was diluted to 100 mL with injectable water, dissolved, filtered, and then the filtrate was placed into a special bottle for nasal spray.

Example 9 Spray Formula

Formula

| Formula | |
| --- | --- |
| Chlorogenic acid | 10 g |
| Polyethylene glycol | 20 g |
| Dilution to 100 mL with normal saline | |

Preparative Method:

Chlorogenic acid, polyethylene glycol, and a small amount of normal saline were weighed according to the formula, and allowed to dissolve under heating, followed by cooling. The resultant solution was diluted to 100 mL with normal saline, dissolved, filtered, and then the filtrate was placed into a special bottle for nasal spray.

The beneficial effects of the present invention was further illustrated by following experimental examples:

Experimental Example 1 Experimental Investigation on the Bioavailability of Nasal Administration in Beagle Dogs

1 Materials and Methods 1.1 Drugs (1) Chlorogenic acid bulk drug; (2) Example 1 nasal powder; (3) Example 5 nasal powder; (4) Example 6 aerosol; (5) Example 7 aerosol; (6) Chlorogenic acid for injection 1.2 Animals Six male beagle dogs, weighing 10-13 kg.

2 Experimental Procedures 2.1 Animal Administration

Six beagle dogs were randomly divided into groups and cross-administered with one week interval.

After fasting for 12 h, test animals were given chlorogenic acid, nasal powder, and aerosol at a dose of 4 mg/kg chlorogenic acid by nasal administration, and one additional dog was injected intravenously with chlorogenic acid at 4 mg/kg. 3 h after administration, dogs were allowed to feed;

2.2 Blood Sample Collection 10 min, 30 min, 60 min, 90 min, 120 min, 150 min after administration of beagle dogs, 3 mL intravenous blood was collected, heparin was used to anticoagulate, and then 1 mL serum was separated by centrifugation, and stored in a refrigerator at −20° C.

2.3 Blood Sample Processing

To 100 μL serum, were added methanol-0.2% phosphoric acid (80:20) solution (100 μL), the solution of puerarin in methanol as internal standard (50 mg/mL, 100 μL), and 100 μL methanol. The resultant solution was vortexed for 3 min, allowed to stand, and centrifuged (12000 rpm) for 10 min. The supernatant was collected as the serum test solution.

2.4 Blood Test

Octadecylsilane-bonded silica gel column (150 mm×4.6 mm, 5 μm) and guard column were used; mobile phase A (methanol) and mobile phase B (0.2% phosphoric acid) were used to perform desorption according to a gradient elution procedure; the detection wavelength was 325 nm; the flow rate was 1 mL/min; the column temperature was 40° C.

| Time (min) | Phase A (%) | Phase B (%) |
| --- | --- | --- |
| 0 | 10 | 90 |
| 17 | 20 | 80 |
| 22 | 40 | 60 |
| 24 | 40 | 60 |

20 μL of the serum test solution was accurately measured, and injected into the liquid chromatograph, to record the chromatogram. The internal standard method was used to calculate the content of chlorogenic acid in serum with accompanying standard curve.

3. Statistical Processing

The experimental data are expressed as mean±standard deviation, and t test was carried out.

4. Experimental Results

The results of chlorogenic acid content in the blood of beagle dogs in each test group at each time point after administration are shown in Table 1 and FIG. 1.

TABLE 1

The results of chlorogenic acid content in the blood of beagle dogs in each test group at each time point after administration

| Experimental groups | Content of chlorogenic acid in the blood of beagle dogs ($\bar{x} \pm s$, μg/mL) | | | | | |
|---|---|---|---|---|---|---|
| | 10 min | 30 min | 60 min | 90 min | 120 min | 150 min |
| Chlorogenic acid bulk drug group | 1.02 ± 0.53 | 5.74 ± 1.32 | 2.20 ± 0.52 | 0.98 ± 0.21 | 0.52 ± 0.14 | 0.22 ± 0.11 |
| Example 1 nasal powder group | 2.27 ± 0.87 | 12.61 ± 4.73 | 8.07 ± 1.28 | 1.52 ± 0.35 | 0.63 ± 0.09 | 0.12 ± 0.06 |
| Example 5 nasal powder group | 1.59 ± 0.54 | 10.02 ± 1.44 | 8.25 ± 0.99 | 3.83 ± 0.86 | 1.11 ± 0.26 | 0.35 ± 0.12 |
| Example 6 aerosol group | 3.51 ± 1.74 | 18.39 ± 4.02 | 7.95 ± 3.73 | 3.22 ± 1.85 | 0.32 ± 0.16 | 0 |
| Example 7 aerosol group | 3.89 ± 0.58 | 15.62 ± 3.52 | 6.37 ± 2.24 | 2.04 ± 1.08 | 0.62 ± 0.83 | 0 |
| Intravenous administration | 23.21 ± 2.14 | 7.56 ± 0.93 | 1.42 ± 0.56 | 0.36 ± 0.22 | 0 | 0 |

5. Conclusion

The results of the blood drug concentration in beagle dogs of each experimental group showed that both nasal powder and aerosol could significantly improve the bioavailability of chlorogenic acid for nasal administration. The highest blood concentration was basically close to that obtained by intravenous injection, and thus the preliminary judgment was that nasal powder and aerosol had similar effects to injections in terms of efficacy.

Experimental Example 2 Experimental Investigation on Blood-Brain Barrier Permeability in Rats after Nasal Administration

1 Materials and Methods 1.1 Drugs (1) Chlorogenic acid; (2) Example 1 nasal powder; (3) Example 5 nasal powder; (4) Example 6 aerosol; (5) Example 7 aerosol 1.2 Animals 150 SD rats, half male and half male, weighing 180-220 g.

2 Experimental Procedures 2.1 Animal Administration

SD rats were randomly divided into 5 groups, 30 rats for each group, and each test drug was administrated nasally at a dose of 20 mg/kg chlorogenic acid. The tissue samples were collected at 10 min, 30 min, 60 min, 90 min, 120 min, and 150 min after administration.

2.2 Brain Tissue Collection

After administration, each experimental group was intraperitoneally injected with 1% pentobarbital sodium (0.2 mL) for deep anesthesia according to the time point, and then a needle was inserted from the left ventricle. The right ventricle was cut, and physiological saline was injected with a syringe for cardiac perfusion until the liver and spleen turned gray, and the brain tissue was taken out.

2.3 Brain Tissue Processing

The brain tissue was placed in a homogenizer, to which was added 0.9% sodium chloride injection according to brain tissue: normal saline=1:1 (w/v) and then homogenized. To 200 μL homogenate, were added 50 mg/mL puerarin internal standard solution (200 μL) and methanol (200 μL), and then the mixture was vortexed and centrifuged. The supernatant was collected as the brain tissue test solution.

2.4 Brain Tissue Detection

Octadecylsilane-bonded silica gel column (150 mm×4.6 mm, 5 μm) and guard column were used; mobile phase A (methanol) and mobile phase B (0.2% phosphoric acid) were used to perform desorption according to a gradient elution procedure; the detection wavelength was 325 nm; the flow rate was 1 mL/min; the column temperature was 40° C.

| Time (min) | Phase A (%) | Phase B (%) |
|---|---|---|
| 0 | 10 | 90 |
| 17 | 20 | 80 |
| 22 | 40 | 60 |
| 24 | 40 | 60 |

20 μL of the brain tissue test solution was accurately measured, and injected into the liquid chromatograph, to record the chromatogram. The internal standard method was used to calculate the content of chlorogenic acid in serum with accompanying standard curve.

3. Statistical Processing

The experimental data are expressed as mean±standard deviation, and t test was carried out.

4. Experimental Results

Figure 2:
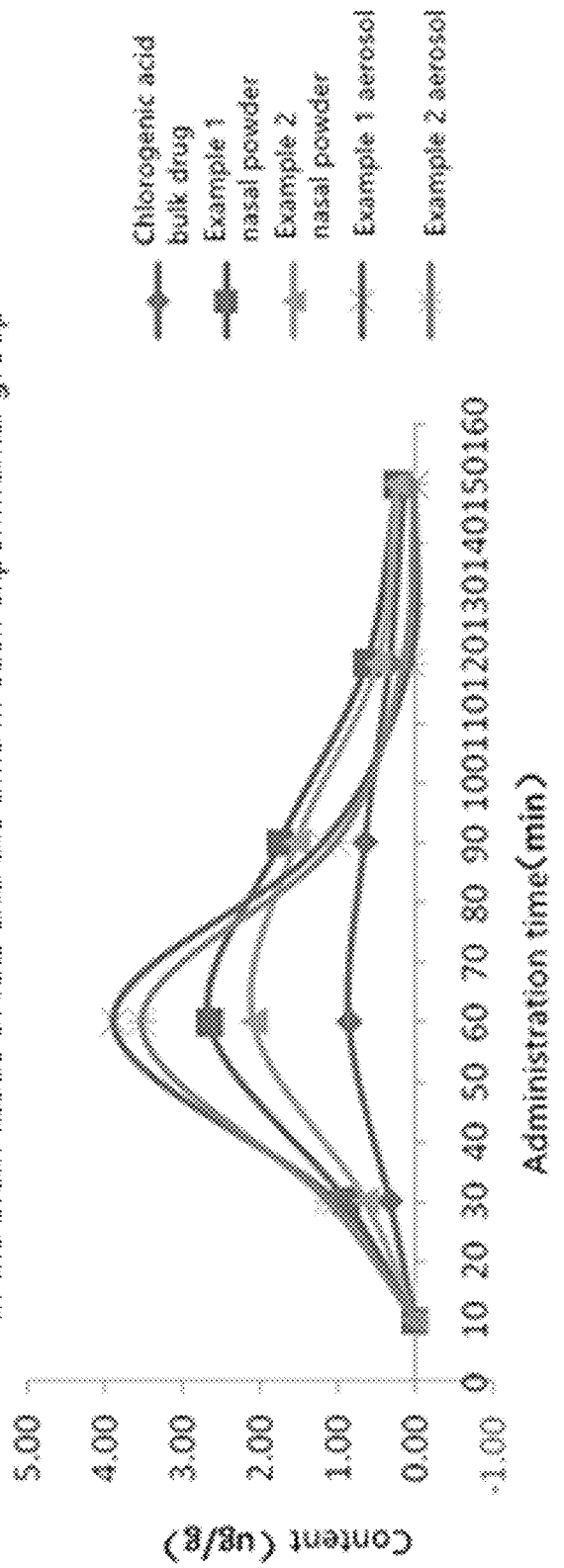
FIG. 2 shows the content of chlorogenic acid in the brain tissue of rats at various time points after the administration of the drugs.

The results of chlorogenic acid content in the brain tissue of rats in each test group at each time point after nasal administration are shown in Table 2 and FIG. 2.

TABLE 2

The results of chlorogenic acid content in the brain tissue of rats in each test group at each time point after nasal administration

| Test groups | The content of chlorogenic acid in the brain tissue of rats ($\bar{x} \pm s$, μg/g) | | | | | |
|---|---|---|---|---|---|---|
| | 10 min | 30 min | 60 min | 90 min | 120 min | 150 min |
| Chlorogenic acid bulk drug group | 0 | 0.32 ± 0.14 | 0.86 ± 0.36 | 0.65 ± 0.25 | 0.32 ± 0.17 | 0.13 ± 0.05 |
| Example 1 nasal powder group | 0 | 0.89 ± 0.08 | 2.65 ± 0.32 | 1.74 ± 0.17 | 0.62 ± 0.15 | 0.22 ± 0.05 |
| Example 5 nasal powder group | 0 | 0.64 ± 0.05 | 2.09 ± 0.75 | 1.53 ± 0.29 | 0.48 ± 0.12 | 0.23 ± 0.09 |
| Example 6 aerosol group | 0 | 1.02 ± 0.11 | 3.88 ± 0.42 | 1.18 ± 0.32 | 0.06 ± 0.03 | 0 |
| Example 7 aerosol group | 0 | 1.13 ± 0.12 | 3.52 ± 0.26 | 1.02 ± 0.12 | 0.15 ± 0.04 | 0 |

5. Conclusion

The test results for the blood-brain barrier permeability showed that aerosols had the highest blood-brain barrier permeability in a short period of time, followed by nasal powders. Chlorogenic acid bulk drugs had lower permeability, indicating that the formulas of nasal powder and aerosol could help chlorogenic acid to penetrate the blood-brain barrier, in which aerosol is the best. This suggested that nasal powder and aerosol had a higher clinical value in the treatment of brain-related diseases.

Experimental Example 3 Comparative Study on the Inhibitory Effect of Nasal Administration and Intraperitoneal Injection on Glioma in Rats

1 Materials and Methods 1.1 Drugs
1.1.1 Test Drugs for Nasal Administration: (1) Chlorogenic Acid Bulk Drug; (2) Example 1 Nasal Powder; (3) Example 5 Nasal Powder; (4) Example 6 Aerosol; (5) Example 7 Aerosol;
1.1.2 Test Drug for Intraperitoneal Injection: Chlorogenic Acid for Injection
1.1.3 Positive Control Drug: Temozolomide
1.2 Animals
40 SD rats, half male and half male, weighing 180-220 g.
1.3 Cell Lines
Rat C6 glioma cells

2 Experimental Procedures 2.1 Cell Culture
Rat C6 glioma cells were incubated in 10% calf serum DMEM complete culture medium, subcultured in a monolayer culture method and allowed to grow to the required number of cells, and then subcultured once before inoculation. Cells in logarithmic growth phase are collected, digested with trypsin, centrifuged, and made to $1 \times 10^4/10$ μL cell suspension with Hanks solution, then stored in a refrigerator at 4° C. for inoculation.
2.2 Seeding and Modeling
Rats were anesthetized by intraperitoneal injection of 10% chloral hydrate, and the hair on the top of the rat's head was cut off and disinfected with iodine. The scalp was cut to expose the skull, and an electronic dental drill was used to open the cranium 1 mm behind the coronal suture and 3 mm to the right of the sagittal suture. 10 μL C6 cell suspension was injected, the bone hole was sealed with bone wax, and the incision was sutured. 5 days after tumor inoculation, the rats were examined by imaging, and tumorigenic rats were selected.
2.3 Animal Administration
The tumorigenic rats were randomly divided into 8 groups, 5 rats for each group, and the groups included nasal administration groups: chlorogenic acid bulk drug group, the nasal powder group of example 1, the nasal powder group of example 5, the aerosol group of example 6, and the aerosol group of example 7; intraperitoneal injection group of chlorogenic acid, temozolomide positive control drug group, and blank group. For nasal administration, each test drug group received corresponding drugs at a dose of 20 mg/kg chlorogenic acid daily; intraperitoneal injection group of chlorogenic acid was administrated at a dose of 20 mg/kg chlorogenic acid daily; temozolomide positive control group was administered intragastrically at a dose of 25 mg/kg daily. Each test group started to be given the drug on the 6th day after tumor inoculation for 20 consecutive days, and on the 21st day each drug group and the blank group were imaged to check the tumor size.

3 Statistical Processing

SPSS software was used to perform t test, analysis of variance and multiple comparisons test. The experimental data were all expressed as mean±standard deviation, and $P<0.05$ indicated that the difference was statistically significant.

4 Experimental Results

The post-processing platform was used to measure the tumor volume on the 3DFSPGR sequence, and the tumor inhibition rate was calculated. The results are shown in Table 3.

TABLE 3

Results for inhibition rate of each drug group on rat brain glioma

| Experimental group | | Tumor size (mm3) | Tumor inhibition rate (%) |
|---|---|---|---|
| Nasal administration | Chlorogenic acid bulk drug group | 48.35 ± 4.83 | 22.35 |
| | Example 1 nasal powder group | 22.25 ± 5.21# | 64.27 |
| | Example 5 nasal powder group | 28.51 ± 2.35# | 54.22 |
| | Example 6 aerosol group | 29.36 ± 4.08# | 52.85 |
| | Example 7 aerosol group | 24.17 ± 3.65# | 61.19 |
| Intraperitoneal injection | Chlorogenic acid group for injection | 36.44 ± 7.09# | 41.48 |
| Intragastric administration | Positive control group | 37.63 ± 3.21# | 39.57 |
| — | Blank group | 62.27 ± 6.48 | — |

Note:
indicates a significant difference from the blank group ($P < 0.05$).

5 Conclusion

Experimental results showed that the tumor inhibition rate for the formula groups of nasal powder and aerosol was both more than 50%, which was better than that of temozolomide positive control group. Compared with the blank group, there was a significant difference (P<0.05). For chlorogenic acid bulk drug group, there was no statistical significance (P>0.05).

Chlorogenic acid group injected intraperitoneally was slightly better than the positive control group of temozolomide, and compared with the blank group, there was a significant difference (P<0.05). The tumor inhibition rates of the formula groups of nasal powder and aerosol for nasal administration were higher than that of chlorogenic acid group for intraperitoneal injection, indicating that giving the same dose of chlorogenic acid, the anti-tumor effect of the formula groups of nasal powder and aerosol for nasal administration on rat C6 glioma cells was better than that of intraperitoneal injection. This suggested that the nasal administration of chlorogenic acid nasal powder and aerosol has a good clinical application prospect in the treatment of glioma.

Experimental Example 4 Experimental Investigation on the Inhibitory Effect of Nasopharyngeal Carcinoma by Intranasal Administration and Intraperitoneal Injection in Rats 1 Materials and Methods 1.1 Drugs
1.1.1 Test Drugs for Nasal Administration: (1) Chlorogenic Acid Bulk Drug; (2) Example 1 Nasal Powder; (3) Example 5 Nasal Powder; (4) Example 6 Aerosol; (5) Example 7 Aerosol;
1.1.2 Test Drug for Intraperitoneal Injection: Chlorogenic Acid for Injection
1.1.3 Positive Control Drug: Retinoic Acid
1.2 Animals
SD rats, half male and half male, weighing 180-220 g.
2. Experimental Procedures
2.1 Inducing and Promoting Cancer SD rats were randomly divided into 8 groups, 5 rats for each group, and the groups included nasal administration groups: chlorogenic acid bulk drug group, the nasal powder group of example 1, the nasal powder group of example 5, the aerosol group of example 6, and the aerosol group of example 7; intraperitoneal injection group of chlorogenic acid, positive control drug group, and blank group. Amongst, for nasal administration, each test drug group received corresponding drugs at a dose of 20 mg/kg chlorogenic acid daily, once a day; intraperitoneal injection group of chlorogenic acid was administrated at a dose of 20 mg/kg chlorogenic acid daily, once a day; retinoic acid positive drug group was administered intragastrically at a dose of 90 mg/kg daily, once a day. Rats in each experimental group were given dinitrosopiperazine and phorbol ester to promote cancer. Dinitrosopiperazine was injected into the armpit at a dose of 40 mg/kg to induce carcinogenesis, twice a week, for a total of 15 weeks. After dinitrosopiperazine was injected for two weeks, phorbol diester was injected at a dose of 50 ng/rat, twice a week, for a total of 15 weeks. The rats were sacrificed at the 20th week, rhinitis tissues were dissected, histopathology was observed, and telomerase was detected.

2.2 Histopathological Observation

Rat nasopharyngeal tissues were fixed with 10% formaldehyde, decalcified in Jenkin's solution, further fixed in neutral formalin, and embedded in paraffin to make serial sections, then stained with hematoxylin and eosin and observed under a microscope.

2.3 Telomerase Detection

Nasopharyngeal tissue homogenate was weighed and centrifuged, and then the supernatant was collected and processed according to Telomerase ELISA-PCR kit instruction (Shanghai Boehringer Mannheim Co.). After obtaining PCR reaction product, the telomerase activity was quantitatively detected, followed by concentration and electrophoresis on polyacrylamide gel, then staining with silver nitrate.

3. Statistical Processing

The experimental data are expressed as mean±standard deviation, and t test was carried out.

4. Experimental Results (1) The results of paraffin microscopy showed that there were two epithelial cancer cells in the nasopharyngeal tissue of the blank group, the basement membrane was intact, and the cancer was judged to be carcinoma in situ. In addition, the number and layer of three epithelial cells increased, the cell morphology was irregular, and deep staining of the nuclear and multiple nuclei were allowed to judge as dysplasia. In the positive control group, the number of local cells in one epithelium increased, the layers of cells increased, and the cell morphology was normal, together with non-nucleus heterogeneous cells, that was allowed to judge as simple hyperplasia; four other epithelial cells were 3-5 layers, the cells were neatly arranged, and the size was the same, that was allowed to judge as a normal tissue. For test drugs for nasal administration, three in the chlorogenic acid raw material group were dysplasia, and for the remaining two, one was simple hyperplasia, and the other was normal tissue. In each test group of nasal powder formula and aerosol formula, except that the nasal powder group of Example 5 and the aerosol group of Example 6 had one simple hyperplasia, and the others were all normal tissues. In the intraperitoneal injection group, one was dysplasia, two were simple hyperplasia, and one was normal tissue. See Table 4 for details.

TABLE 4

Results of nasopharyngeal tissue paraffin microscopy

| Mode of administration | Experimental groups | Normal tissue | Simple hyperplasia | Dysplastic tissue | Cancerous tissue |
|---|---|---|---|---|---|
| Nasal administration | Chlorogenic acid bulk drug group | 1 | 1 | 3 | — |
| | Example 1 nasal powder group | 5 | — | — | — |
| | Example 5 nasal powder group | 4 | 1 | — | — |
| | Example 6 aerosol group | 4 | 1 | — | — |
| | Example 7 aerosol group | 5 | — | — | — |
| Intraperitoneal injection | Chlorogenic acid group for injection | 2 | 2 | 1 | — |
| Intragastric administration | Retinoic acid positive control group | 4 | 1 | — | — |
| — | Blank group | — | — | 3 | 2 |

(2) The telomerase detection results showed that the telomerase activities of the nasal powder and aerosol formulas were lower (0.21±0.09), which was basically the same as the telomerase activity of the retinoic acid positive control group (0.22±0.12) ($P>0.05$); there were significant differences ($P<0.05$), compared with chlorogenic acid bulk drug group (0.56±0.17), intraperitoneal injection group (0.41±0.58), and blank group (0.86±0.21).

5. Conclusion

The formula groups of nasal powder and aerosol by nasal administration can effectively block the process of nasopharyngeal carcinogenesis in rats, and it is significantly different from the chlorogenic acid bulk drug group, and is better than the intraperitoneal injection. The drug effect is almost identical to that of retinoic acid positive control drug, and the results indicated that the nasal powder and aerosol of the present invention could effectively improve the bioavailability of chlorogenic acid for nasal administration, have more significant effects in the treatment of nasopharyngeal carcinoma, and can be used as clinical drugs.

In summary, chlorogenic acid preparation of the present invention for nasal administration could improve the bioavailability of chlorogenic acid by nasal administration, penetrate the blood-brain barrier, has a significant inhibitory effect on brain tumors and nasopharyngeal carcinoma, and has clinical application value.

The invention claimed is:

1. An anti-tumor composition for nasal administration that is a preparation comprising chlorogenic acid as an active ingredient and pharmaceutically acceptable excipients or auxiliary ingredients suitable for nasal administration, wherein:
   said preparation is nasal powder;
   the excipients of said nasal powder are adhesive and absorption enhancer;
   said nasal powder comprises 10-90 parts of chlorogenic acid, 5-80 parts of the adhesive, and 0-70 parts of the absorption enhancer;
   the adhesive is selected from one or more of carbomer, chitosan, and polyvinylpyrrolidone; and
   the absorption enhancer is selected from one or more of lecithin and cholic acid sodium.

2. The composition according to claim 1, wherein the particle size of said nasal powder is 20-100 μm.

3. An anti-tumor composition for nasal administration that is a preparation comprising chlorogenic acid as an active ingredient and pharmaceutically acceptable excipients or auxiliary ingredients suitable for nasal administration, wherein:
   said preparation is aerosol containing 0.1-1 g chlorogenic acid per 1 mL;
   the excipients of said aerosol are propellant, cosolvent and absorption enhancer;
   the excipients comprises 5-30 parts by weight of the propellant, 10-50 parts of the cosolvent, and 1-10 parts of the absorption enhancer;
   the propellant is selected from any one or more of dichlorodifluoromethane and trichlorofluoromethane;
   the cosolvent is selected from any one or more of ethanol, glycerin, and propylene glycol; and
   the absorption enhancer is selected from any one or more of azone, sodium ethylenediaminetetraacetate, and oleic acid.

4. The composition according to claim 3, wherein the excipient of said aerosol further comprises water for injection.

5. A method for preparing the composition according to claim 1, comprising:
   The absolute ethanol or aqueous ethyl acetate is added to the mixture of chlorogenic acid and the absorption enhancer to dissolve, followed by drying and pulverization, then adhesive is added, and the mixture is thoroughly mixed and passed through a 120-1000 mesh sieve to obtain the composition; or
   Chlorogenic acid, absorption enhancer, and adhesive are mixed, and passed through a 120-1000 mesh sieve to obtain the composition; or
   Chlorogenic acid, cosolvent and a small amount of solvent are heated to dissolve, and then cooled, to which are further added propellant, absorption enhancer and remaining solvent to dissolve, followed by filtration, and the filtrate is collected to obtain the composition; or
   Chlorogenic acid, polyethylene glycol and a small amount of solvent are heated to dissolve, and then cooled, to which is added the remaining solvent, mixed, filtered, and the filtrate is collected to obtain the composition.

6. A drug for improving the permeability of the blood-brain barrier of chlorogenic acid, comprising the composition according to claim 1.

7. The drug according to claim 6, wherein said drug is those for alleviation and/or treatment of nasopharyngeal carcinoma or brain tumor.

8. The drug according to claim 6, wherein said brain tumors are malignant.

9. The drug according to claim 6, wherein said malignant brain tumors are glioblastoma, ependymoma, or oligodendrocytoma.

* * * * *